(12) United States Patent
Soroudi

(10) Patent No.: US 8,267,907 B2
(45) Date of Patent: Sep. 18, 2012

(54) DEVICE AND METHOD FOR EXOTHERMIC TREATMENT OF EYELID DISEASES

(76) Inventor: Abraham Ebbie Soroudi, Los Angeles, CA (US)

( * ) Notice: Subject to any disclaimer, the term of this patent is extended or adjusted under 35 U.S.C. 154(b) by 0 days.

(21) Appl. No.: 11/740,856

(22) Filed: Apr. 26, 2007

(65) Prior Publication Data

US 2007/0203462 A1    Aug. 30, 2007

Related U.S. Application Data

(63) Continuation of application No. 10/799,209, filed on Mar. 12, 2004, now Pat. No. 7,211,070.

(60) Provisional application No. 60/526,251, filed on Dec. 1, 2003.

(51) Int. Cl.
*A61M 35/00*    (2006.01)

(52) U.S. Cl. .......................... 604/294; 604/289

(58) Field of Classification Search .......... 604/289–291, 604/294–296; 607/109
See application file for complete search history.

(56) References Cited

U.S. PATENT DOCUMENTS

| | | | |
|---|---|---|---|
| 2,527,947 A | 10/1950 | Loos | |
| 2,573,791 A | 11/1951 | Howells | |
| 2,765,789 A | 10/1956 | Schmierer | |
| 3,762,419 A | 10/1973 | Walters | |
| 3,804,077 A | 4/1974 | Williams | |
| 4,134,401 A | 1/1979 | Galician | |
| 4,268,272 A * | 5/1981 | Taura | 44/253 |
| 4,372,318 A | 2/1983 | Viesturs et al. | |
| 4,516,564 A * | 5/1985 | Koiso et al. | 126/263.02 |
| 4,666,441 A | 5/1987 | Andriola et al. | |
| 4,995,114 A | 2/1991 | Price, Jr. | |
| 5,389,066 A | 2/1995 | Rhame, Jr. | |
| 5,456,704 A | 10/1995 | Kilcullen | |
| 5,769,806 A | 6/1998 | Radow | |
| 5,879,378 A * | 3/1999 | Usui | 607/96 |
| 6,090,060 A | 7/2000 | Radow | |
| 6,149,615 A | 11/2000 | Gallamore | |
| 6,261,595 B1 | 7/2001 | Stanley et al. | |
| 6,409,746 B1 * | 6/2002 | Igaki et al. | 607/109 |
| 6,436,128 B1 | 8/2002 | Usui | |
| 6,623,517 B1 | 9/2003 | DeLuisa et al. | |
| 6,629,964 B1 * | 10/2003 | Ono et al. | 604/304 |
| 2003/0056281 A1 | 3/2003 | Hasegawa | |
| 2004/0074502 A1 | 4/2004 | Abbasi | |
| 2005/0022823 A1 | 2/2005 | Davison et al. | |
| 2006/0018953 A1 | 1/2006 | Guillon et al. | |

FOREIGN PATENT DOCUMENTS

WO    WO 93/10019    5/1993

* cited by examiner

*Primary Examiner* — Michele M Kidwell
(74) *Attorney, Agent, or Firm* — Blakely, Sokoloff, Taylor & Zafman, LLP

(57) ABSTRACT

Provided herein is a pad for treating the eye comprising a container having an impermeable outer membrane sized to fit generally within the peri-orbital region and sufficiently flexible to mold to the eye; a first chemical in the container; a second chemical in the container, the first and second chemicals selected to have an exothermic reaction for producing heat suitable for treating the eye, the exothermic reaction providing the suitable temperature for a period of time suitable for treating the eye. The container is covered with a soft, non-abrasive, lint-free material which may be presoaked in a pH controlled soap with or without an antibiotic. Other embodiments are also described.

8 Claims, 3 Drawing Sheets

DEVICE AND METHOD FOR EXOTHERMIC TREATMENT OF EYELID DISEASES

RELATED APPLICATION INFORMATION

This Application is a Continuation of Ser. No. 10/799,209, filed on Mar. 12, 2004, now U.S. Pat. No. 7,211,070 entitled "Device and Method for Exothermic Treatment of Eyelid Diseases" (pending), which is a non-provisional application of U.S. Provisional Application Ser. No. 60/526,251, filed Dec. 1, 2003.

There is a myriad of common eye diseases known in the field of Ophthalmology that necessitate the regular use of warm compresses applied to the periocular skin. The current gold standard of treatment for these conditions includes the simultaneous use of heat to unclog the openings of the eyelid sebaceous glands and increase blood flow to the affected areas, while massaging the eyelids with a non-irritating baby shampoo to wash off oily debris. A bacteriostatic antibiotic ointment is optionally used to cleanse the bacterial flora that reside at the eyelid margin and are believed to lead to these conditions. This set of steps has been proven to treat many of these conditions listed below and is currently the preferred means of achieving proper eyelid hygiene.

Eye diseases which can be treated in this manner include, but are not limited to, acutely infected/inflamed internal or external hordeola or chalazia (Styes), any form of microbio-allergic disease (blepharitis, blepharoconjunctivitis, or conjunctivitis), any eyelid skin rash (e.g., as caused by Herpes Simplex/Zoster Virus, or contact dermatitis), orbital or pre-septal cellulitis, acute dacryocystitis, meibomitis, dry eye syndrome, meibomian gland dysfunction, ocular rosacea, Staphylococcal hypersensitivity, contact lens related ocular irritation, cat-scratch disease, oculoglandular tularemia, and conjunctival tuberculosis or syphilis.

The inconvenience of this ritual is a common cause of poor compliance (and treatment failure) frequently encountered in clinical practice. Patients often use a warm tea-bag or a warm towelette that they hold under warm running water, both of which lose heat within mere seconds. Some run their eyes under hot tap water or try microwave-heated compresses with resulting second-degree burns severe enough that they have even been reported in the scientific literature (Eisman et al., *Opthal. Plast. Reconstr. Sturg.* 2000 July; 16(4):304-5). Needless to say, these methods of applying heat are not lengthy enough to be effective, and can be hot enough to be harmful to the delicate ocular adnexa.

Some users advocate the use of a boiled egg or a warm potato or rice wrapped in a thin towel to provide heat for a longer duration of time. This exercise is quite cumbersome, and may still burn the thin eyelid skin because of high and uncontrolled temperatures.

Also, many ophthalmologists recommend Q-tip applicators be used to scrub the eyelids and lashes with baby shampoo. Not only is this exercise tedious and inconvenient for even young, healthy individuals, but is quite a difficult task for the elderly, especially those who suffer from arthritis, those who fatigue easily, have poor near visual acuity, or those whose hands shake.

SUMMARY OF THE INVENTION

In one aspect of the present invention, the ritual of frequent use of warm compresses, scrubbing the lids with baby shampoo, and applying antibiotic ointment, is replaced with a much more convenient procedure, which combines these three steps into one. In one embodiment, a product is provided that makes treating those affected by the aforementioned eye diseases more convenient, effective, and safe.

In another aspect of the present invention, a convenient product promotes better eyelid hygiene by making this exercise less tedious, thereby preventing the occurrence and/or recurrence of the underlying problem. In a preferred aspect of the present invention, compliance with the best medical treatment for these conditions is enhanced through ease of use.

In yet another aspect, a convenient method for reducing the potential infectious complications of intraocular surgery is provided.

In another preferred aspect, the invention provides pain relief to sufferers of certain conditions of the eye, such as dry eyes, or post-surgical pain.

DETAILED DESCRIPTION

In a first aspect, the disclosure shows an eye pad that provides heat, a cleansing material, and an antibacterial substance, wherein the eye pad is sufficiently flexible to conform to the peri-orbital region, yet sufficiently stiff to be rolled over that area. As used herein, the term "impermeable" means that the contents of the container that is created by the impermeable membrane cannot pass through that membrane under ordinary use of the system. The term "permeable" means that the contents of adjoining compartments separated by the permeable membrane can mix with each other by passage through the permeable membrane. In a particular embodiment, the separating membrane is rendered permeable by breakage of the membrane. The term "membrane" refers to a flexible or inflexible barrier.

Figure 1:
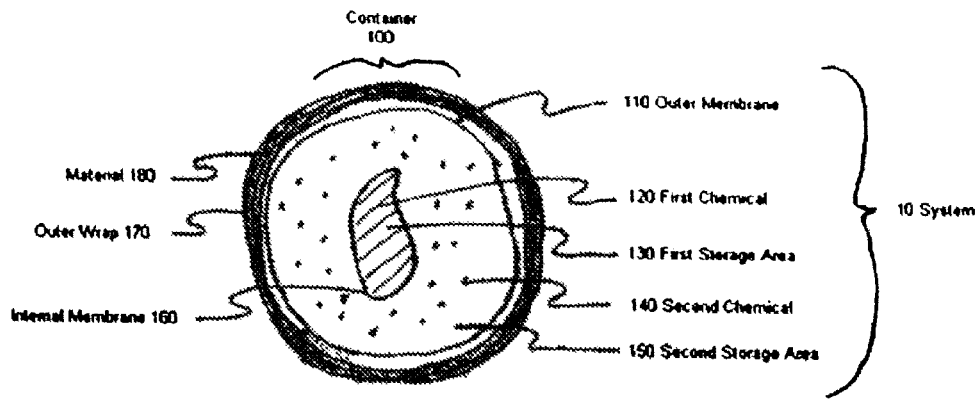
FIG. 1 shows a cross sectional view of an eye pack.

Referring now to FIG. 1 which shows eye pad system 10, multipart container 100 having impermeable outer membrane 110 is sized to fit generally within a user's peri-orbital region, and is sufficiently flexible to mold to that region of the user's face. First chemical 120 is stored in first, inner, concentric storage area 130 of multipart container 100. Second chemical 140 is stored in second, outer, concentric storage area 150 of multipart container 100. The first and second chemicals have been chosen to cause an exothermic reaction when mixed. Internal membrane 160 separates the first and second chemicals in container 100. Internal membrane 160 can be rendered permeable through such actions as the application of physical force to container 100, while at the same time impermeable outer membrane 110 maintains its impermeability.

Figure 7:
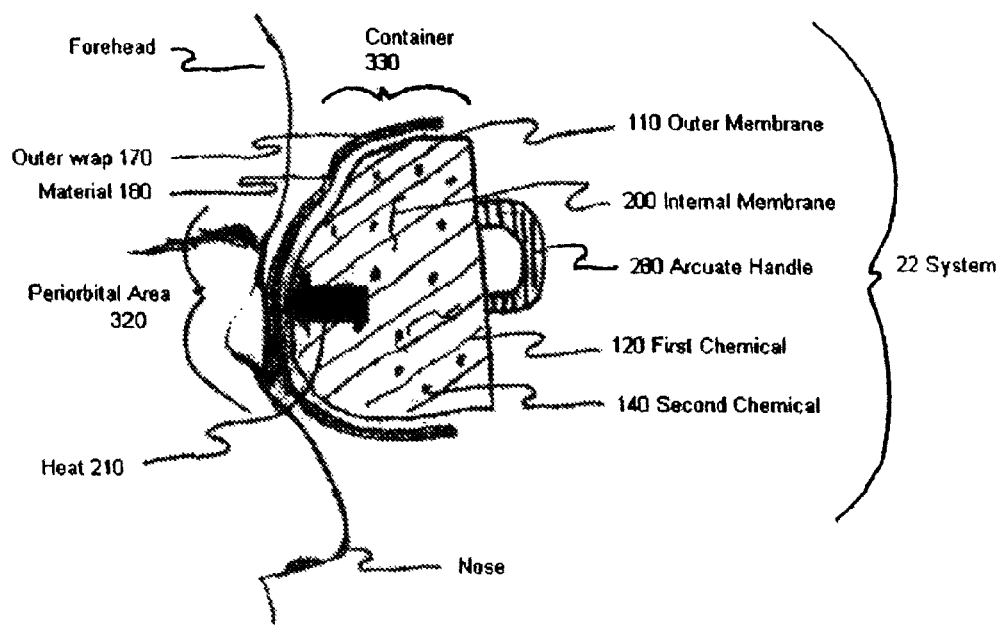
FIG. 7 shows an eye pad on the peri-orbital region.

Outer wrap 170 covers at least part of impermeable outer membrane 110 and is attached at enough places to create a smooth surface at least the size of the peri-orbital region. Outer wrap 170 may completely cover multipart container 100, or it may cover a smaller part of container 100, such as the portion of impermeable outer membrane 110 that would otherwise come in contact with the user's face, as shown in FIG. 7. Outer wrap 170 is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Figure 2:
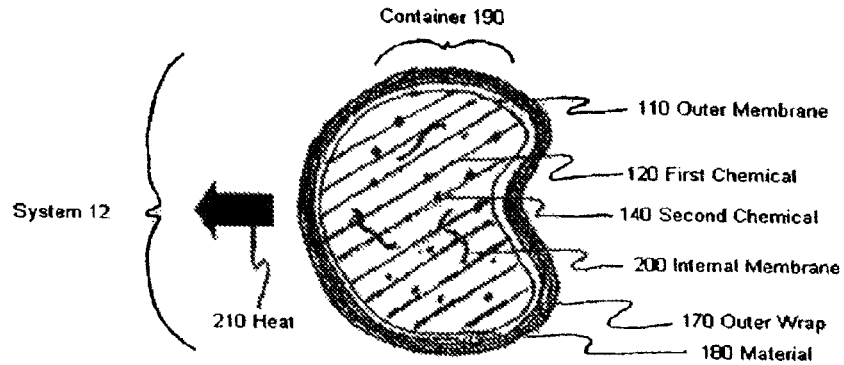
FIG. 2 shows the cross sectional view of the eye pack with burst inner membrane and resulting exothermic reaction.

Referring now to FIG. 2 and eye pad system 12, container 190 having impermeable outer membrane 110 is sized to fit generally within a user's peri-orbital region, and is sufficiently flexible to mold to the eye region of the user's face. Internal membrane 200 has been rendered permeable by rupture. First chemical 120 and second chemical 140 are mixed in container 190. The first and second chemicals have been chosen to cause an exothermic reaction when mixed, releasing heat 210 from the system 12. Impermeable outer membrane 110 remains impermeable when internal membrane 200 is rendered permeable. Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Figure 3:
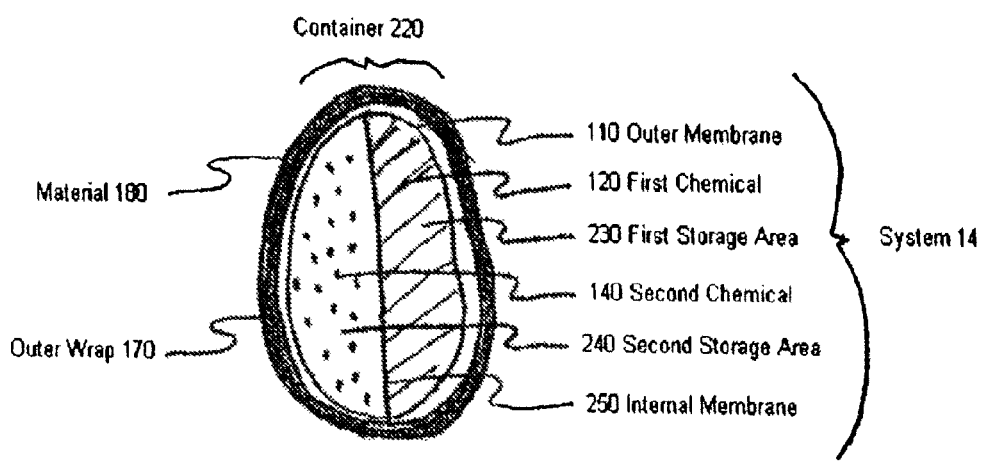
FIG. 3 shows an alternative cross sectional view of the exothermic heat pack.

FIG. 3 is similar to FIG. 1, showing an eye pad system 14 having multipart container 220 with impermeable outer membrane 110 that is sized to fit generally within a user's peri-orbital region, and is sufficiently flexible to mold to the eye region of the user's face. First chemical 120 is stored in first adjacent storage area 230 of multipart container 220. Second chemical 140 is stored in second adjacent storage area 240 of multipart container 220, abutting first adjacent storage area 230. The first and second chemicals have been chosen to cause an exothermic reaction when mixed. Internal membrane 250 that can be rendered permeable, separates the first and second chemicals in container 220. Internal membrane 250 can be rendered permeable through such actions as the application of physical force to container 220 while at the same time the impermeability of outer membrane 110 is maintained. Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to deanse the region.

Figure 4:
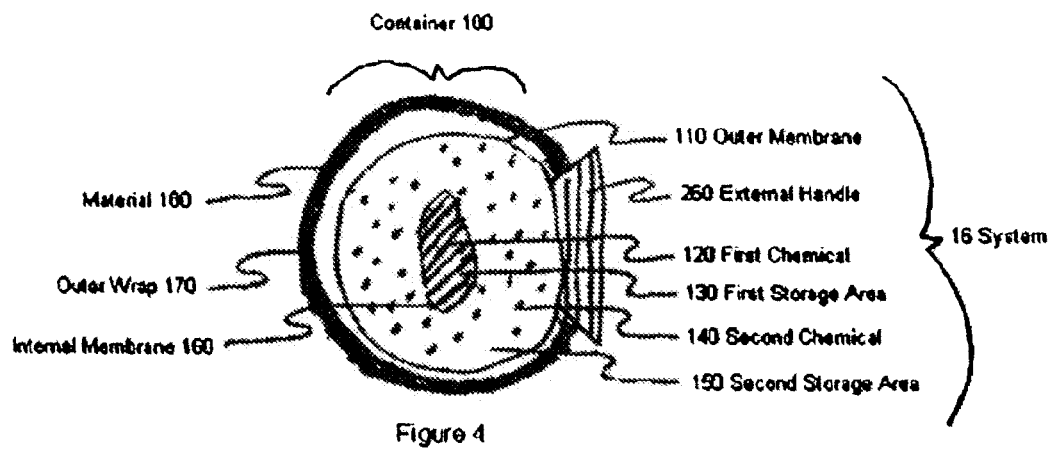
FIG. 4 shows a cross sectional view of an exothermic heat pack with an external handle.

Referring now to FIG. 4 and eye pad system 16, multipart multipart container 100 having impermeable outer membrane 110 is sized to fit generally within a user's peri-orbital region, and is sufficiently flexible to mold to that region of the user's face. First chemical 120 is stored in first, inner, concentric storage area 130 of multipart container 100. Second chemical 140 is stored in second, outer, concentric storage area 150 of multipart container 100. The first and second chemicals have been chosen to cause an exothermic reaction when mixed. Internal membrane 160 separates the first and second chemicals in container 100. Internal membrane 160 can be rendered permeable through such actions as the application of physical force to container 100 while at the same time the impermeability of outer membrane 110 is maintained.

Outer wrap 170 covers at least part of impermeable outer membrane 110 and is attached at enough places to create a smooth surface at least the size of the peri-orbital region. Outer wrap 170 may completely cover multipart container 100, or it may cover a smaller part of container 100, such as the portion of impermeable outer membrane 110 that would otherwise come in contact with the user's face, as shown in FIG. 7. Outer wrap 170 is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

External handle 260 can be rigidly attached to impermeable outer membrane 110 to provide a convenient way for a user to hold the eye pad. External handle 260 is also useful in the manual rupture of internal membrane 160 by providing a means for grasping and pushing firmly on outer membrane 110. Likewise, external handle 260 can be useful in the manipulation of system 16, especially around the peri-orbital region.

Figure 5:
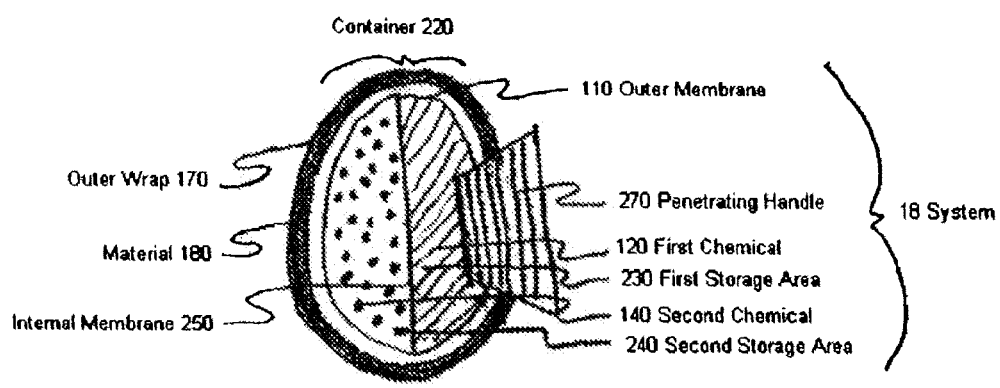
FIG. 5 shows a cross sectional view of an alternative exothermic heat pack with a penetrating handle.

Referring now to FIG. 5, and eye pad system 18, multipart container 220 with impermeable outer membrane 110, is sized to fit generally within a user's peri-orbital region, and is sufficiently flexible to mold to the eye region of the user's face. First chemical 120 is stored in first adjacent storage area 230 of multipart container 220. Second chemical 140 is stored in second adjacent storage area 240 of multipart container 220, abutting first adjacent storage area 230. The first and second chemicals have been chosen to cause an exothermic reaction when mixed. Interior membrane 250 that can be rendered permeable, separates the first and second chemicals in container 220. Internal membrane 250 can be rendered permeable through such actions as the application of physical force to container 220 while at the same time the impermeability of outer membrane 110 is maintained. Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for cleansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Penetrating handle 270 can be rigidly attached to impermeable outer membrane 110 to provide a convenient way for a user to hold the eye pad. The presence of a portion of penetrating handle 270 inside first storage area 230 adds further stability to penetrating handle 270. Penetrating handle 270 is useful in the manual rupture of internal membrane 250 by providing a means for grasping and pushing firmly on outer membrane 110. Likewise, penetrating handle 270 can be useful in the manipulation of system 18, especially around the peri-orbital region.

Figure 6:
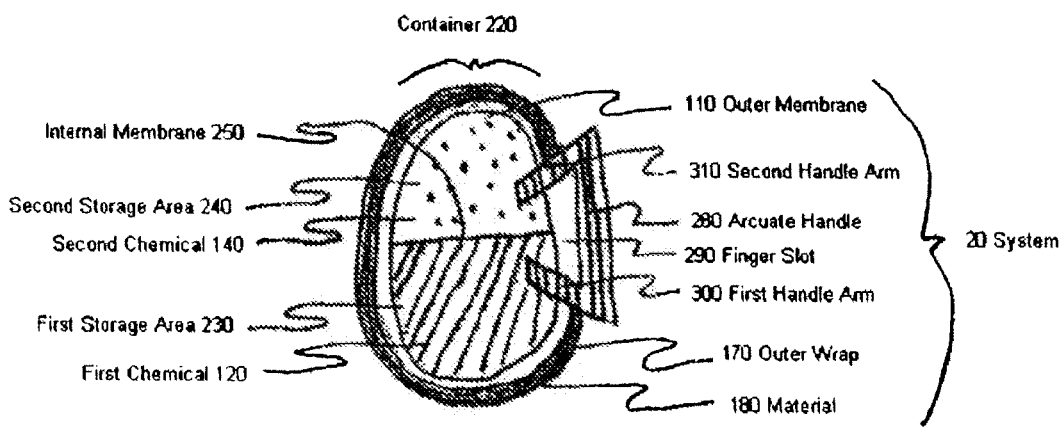
FIG. 6 shows a cross sectional view of an exothermic heat pack with an arcuate handle.

Referring now to FIG. 6, and eye pad system 20, multipart container 220 with impermeable outer membrane 110, is sized to fit generally within a user's peri-orbital region, and is sufficiently flexible to mold to the eye region of the user's face. First chemical 120 is stored in first adjacent storage area 230 of multipart container 220. Second chemical 140 is stored in second adjacent storage area 240 of multipart container 220, abutting first adjacent storage area 230. The first and second chemicals have been chosen to cause an exothermic reaction when mixed. Interior membrane 250 that can be rendered permeable, separates the first and second chemicals in container 220. Internal membrane 250 can be rendered permeable through such actions as the application of physical force to container 220 while at the same time the impermeability of outer membrane 110 is maintained.

Outer wrap 170, which covers at least the area to be placed on the user's face (see FIG. 7), is made of soft, non-abrasive, lint-free material 180 such as gauze. Material 180 is suitable for absorbing and retaining a cleansing substance suitable for deansing the peri-orbital region. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around the peri-orbital region to cleanse the region.

Arcuate handle 280, having finger slot 290 allows a user's fingers to wrap around and better hold arcuate handle 280. Arcuate handle 280 can penetrate into first adjacent storage area 230 with one arm 300, and into second adjacent storage area 240 with the other arm 310. Outer membrane 110 can be sealingly attached to the sides of arcuate handle 280, to maintain the impermeability of container 220. Alternatively, the arms of arcuate handle 280 can be attached to the exterior of outer membrane 110.

FIG. 7 shows the application of an eye pad such as described herein to peri-orbital region 320 of a user. Referring now to eye pad system 22, container 330 having an impermeable outer membrane 110 is sized to fit generally within a user's peri-orbital region 320, and is sufficiently flexible to mold to the eye region of the user's face. Internal membrane 200 has been rendered permeable by rupture. First chemical 120 and second chemical 140 are mixed in container 330. The first and second chemicals have been chosen to cause an exothermic reaction when mixed, releasing heat 210 from the system 22. Impermeable outer membrane 110 remains impermeable when internal membrane 200 is rendered permeable.

Outer wrap 340, which covers the area to be placed on the user's face but does not cover the complete outer membrane 110, is made of soft, non-abrasive, lint-free material 180 such as gauze. Material 180 is suitable for absorbing and retaining a cleansing substance suitable for deansing peri-orbital region 320. Material 180 is also suitable for absorbing and retaining a topical non-allergenic bacteriostatic or bactericidal antibiotic. Material 180 is also flexible in the region to be applied to the face so that the contained cleanser and/or antibiotic can be moved around peri-orbital region 320 to cleanse the region.

Arcuate handle 280 is attached to outer membrane 110 on the side of system 22 opposite that to be applied to the user's face. Arcuate handle 280 can aid in applying pressure to rupture an intact internal membrane to result in internal membrane 200, and can assist user in holding system 22 at or around peri-orbital region 320. To further aid the user in handling system 22, the portion of container 330 facing away from the facial-contact region, and to which arcuate handle 280 is affixed, can be firmer and less flexible than the facial-contact region.

Figure 8:
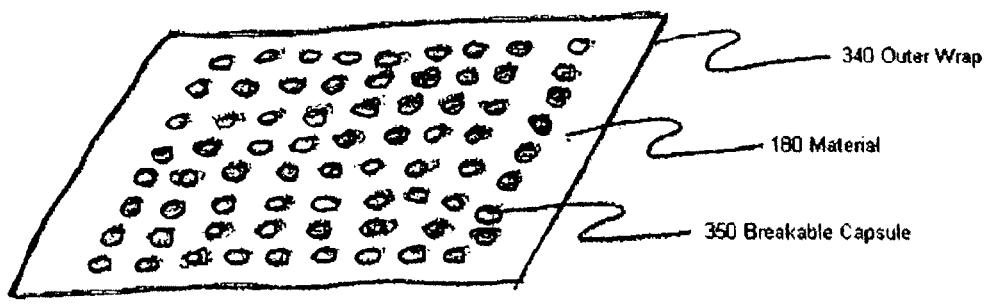
FIG. 8 shows a material that contains cleansing and/or antibiotic in breakable capsules.

FIG. 8 provides an example of outer wrap 340. In this embodiment, small breakable capsules 350 are contained in material 180. Each capsule 350 holds cleansing material, antibiotic, or a combination thereof. Each capsule 350 can be broken, such as by the same application of pressure used to cause internal membrane 160 or 250 to be rendered permeable. Capsules 350 then release their contents into material 180, to be massaged onto the skin of the peri-orbital region 320. This embodiment is especially useful when the cleansing material and/or the antibiotic needs to be protected from the air in order to prolong its life.

In a preferred embodiment, the invention provides a one step treatment of a variety of conditions of the eyelid region. Instead of relying on three separate elements, all three are joined into one device. As a result, when in use, the heat element can combine with the wash and antibiotic to create a better and more efficient result.

It is thought that in treating the aforementioned conditions, the provided heat causes the clogged meibomian gland orifices (which drain behind the insertions of the eyelashes at the eyelid margin) to widen. This allows the viscous (infected) meibomian discharge to drain more easily, while drawing detergent and antibiotic into the openings of these orifices. This exercise improves the viscosity of the oily meibomian discharge, destroys the abnormal microbacterial flora that has lead to the overall poor hygiene of these orifices, and ultimately relieves the blockage. Performed separately, the lid scrubs are not as effective as without the heat, the gland orifices are clogged and narrowed due to the residing abnormal bacterial flora and the resulting inflammation, and the detergent and antibiotic molecules do not penetrate as easily.

A preferred embodiment of the invention is comprised of a heat source, which utilizes an exothermic chemical reaction, supplied in a small, flexible container to be applied over the eyelids; the exothermic reaction produces heat when two different ingredients contained within the container are intermixed.

In one embodiment, a small outer container is made of an air-tight bag or other flexible container, for example made from plastic or silicone. The first container is filled with one of the two ingredients of an exothermic chemical reaction. Inside this outer container, there is another smaller, tightly-sealed, breakable sack, which contains the second ingredient (FIG. 1). This pack includes or is wrapped with a soft material that is preferably lint-free and/or non-abrasive (e.g. gauze, lint-free cotton or other such material), which has been or is then presoaked in a mild, non-irritating antibacterial detergent and a topical non-allergenic bacteriostatic or bactericidal antibiotic.

Before use, the consumer applies pressure to the inner bag (through the outer container) causing it to break, thereby mixing the two necessary ingredients and initiating the exothermic reaction (FIG. 2). The heat pack is then massaged over the eyelids for the duration of the exothermic phase of the reaction. The temperature of the heat source is controlled and remains approximately the same for a desired period of time. The surface of the covering material that comes in contact with the skin includes a gentle detergent and/or an antibacterial solution. This solution or combination of solutions can be present on the surface when the product is unwrapped, or one or more containers of the solution(s) can be provided, into which the unwrapped heat pack is dipped prior to use.

The combination of these elements is a flexible product for placement on the periocular region for treating or preventing a variety of the aforementioned conditions that commonly affect the eyelids.

Uses

This product may be utilized in any of the conditions of the eyelids in which the use of heat has been indicated. The etiology may be infectious (e.g., blepharitis, meibomitis, acute dacryocystitis, orbital or preseptal cellulitis); inflammatory (e.g., inflamed hordeola, chalazia, or contact dermatitis), or combinations thereof. Additionally, dry-eyes, such as caused by wearing contact lenses, can be treated in this manner.

Ocular infection (endophthalmitis) is the most feared complication of any ocular operation (e.g., cataract extraction, corneal transplantation, laser in-situ keratomileusis (LASIK), or glaucoma surgery) (Aaberg T M Jr., et al., *Ophthalmology* 1998 June; 105(6):1004-1010). Intra-operative contamination of the surgical field with the bacteria that usually reside on the eyelashes and the eyelid margins has been found to be a major nidus for infection (Speaker M G et al., *Ophthalmology* 1991 May; 98(5):639-49). As a result, proper eyelid hygiene has become an absolute prerequisite to any intraocular procedure, and a gold standard of ophthalmic surgery today. The various products of the invention are applicable toward this end, and help reduce the possibility of complications that may arise from operating on an eye with existing, poorly-treated blepharitis.

The products are also useful following any intra- or extraocular surgery to provide for symptomatic relief as well as to provide a clean sterile environment until the fresh wounds re-epithelialize, further reducing any chance of infection.

Eyelid edema and/or hematomas resulting from orbital contusion injuries are resolved faster with the use of any of the products of the invention (after an initial 48-hour period of using ice to minimize the initial phase of the inflammatory response).

Heat Source

The heat source is provided by a small, flexible container as described above. Both temperature and duration of the heat production are controlled so as to provide sufficient heat without damaging tissue. For instance, it is extremely important that the maximum temperature reached not be so high as to burn the skin. The temperature and length of time of the reaction can be controlled by the choice of chemicals used to create the reaction, and by the amount of the chemical in each pouch prior to mixing. For the present embodiment of the invention, the preferred temperature is 100-108 degrees Fahrenheit (38-42° C.), as this is the maximum threshold temperature not to cause any thermal injury to the skin (a total delivery of less than 16J/cm$^2$).

Additionally, in the present embodiment, the temperature remains within the desired range for a minimum period of about 5 minutes, preferably about 10-15 minutes. This period of time increases the tear lipid layer thickness by 80%. It is important, however, that the duration of heat application be longer than a mere 20-60 seconds, which is what is available in prior art methods.

In a preferred embodiment, the compounds used to create the exothermic reaction are inert and/or not irritating to skin so that no injury occurs in case the impermeable outer membrane breaks and releases the compounds. It is also preferred strongly that the compounds be environmentally friendly so that the products can be easily and safely disposed of after use.

Structure

In one preferred embodiment, one pouch is contained inside of the second pouch, as is shown in FIGS. 1-3. Although these figures show the eye pad as spherical, it can take any shape as long as it is flexible enough to mold to the approximate shape of the user's peri-orbital region.

In the example shown in these figures, one of the substances is a liquid while the other is a powder, although other forms are acceptable. When the membrane between these compounds is broken, the two ingredients intermix to initiate the exothermic reaction and release adequate heat energy to rapidly raise the temperature of the eye pad to the desired level, and to maintain the reaction for the desired period of time or longer.

In another preferred embodiment, the pouches abut each other, as shown in FIG. 4. Examples of the breakable membrane include but are not limited to plastics, silicone and combinations thereof.

Chemical Reaction

Examples of combinations that will work in the described embodiments to create exothermic reactions include water plus magnesium sulfate, and liquid sodium acetate trihydrate plus stainless steel (aluminum). Other combinations that result in the appropriate temperature and that have reactions that maintain the temperature for the desired period of time are also included.

Shape

The pouch is sufficiently flexible to fit within the user's peri-orbital region, with little or no overlap to the rest of the face. This allows application of heat to the desired area without overlapping onto areas that do not need the treatment. Further, it allows the pouch to be more flexible, and more easily handled.

A handle, such as one made of lightweight but sturdy plastic, can be used as part of the eye pad. The handle is placed away from the portion of the eye pad that will contact skin. Preferably it is placed away from any cleansing material. The handle can be of any shape or construction that enables the user to easily hold the eye pad in place for the prescribed period of time. Examples are shown in FIG. 4.

The pouches are preferably disposable. They can be made of lightweight low-cost materials that need not withstand long periods of use, and are therefore inexpensive and easy to handle for the user.

Cleaning

In addition to the heat source, the pouch contains a cleansing material to clean the periocular region. The material is present on the outside of the pouch so as to be next to the skin. The pouch may be wrapped in a soft, non-abrasive, lint-free material; may have a section of such material attached to it on the side that will be in direct contact with the skin; may be composed of such material; or may have the material provided in any other manner that will allow the material to contact the peri-orbital skin.

In a preferred embodiment, a cleansing substance that is gentle to the skin yet thoroughly cleanses the area is present in the material. Alternatively, a container of such a solution can be supplied with the pouch, to be applied to the material prior to placing the pouch on the skin. In yet another embodiment, the cleanser can be packaged within the material, for example using small breakable cells containing the cleanser, and released by pressure such as is used to initiate the exothermic reaction.

Cleansers can include, but are not limited to any detergent that has been pH controlled not to cause any ocular irritation or cause harm to the cornea if it gets into the eye. One preferred example is baby shampoo. Preferably the cleanser has antibacterial qualities that can improve the removal of bacterial flora from the treatment area.

Antibiotic

In another preferred embodiment, a topical bacteriostatic or bactericidal antibiotic is also present. As with the cleanser, the antibiotic can be supplied in or on the material or packaged within the material. Alternatively, it can be supplied separately, alone or mixed with the cleanser, to be applied to the material prior to placement of the pouch on the skin.

Any antibiotic that can reduce the number of bacterial colonies residing in the peri-ocular adnexa can be used. Antibiotic solutions can include, but are not limited to, Bacitracin, Erythromycin, Gentamicin, Neomycin, Chloramphenicol, and combinations thereof, as the eyelid bacterial flora has been found to be most susceptible to these agents (Dougherty JM et al. *Br. J. Ophthalmol.* 1984 68:524). Bacitracin and Erythromycin ophthalmic ointments are preferred because they have a wide spectrum of activity and are usually very well tolerated. Topical fluoroquinolones, such as, but not limited to, Ciprofloxacin, Norfloxacin, Ofloxacin, and Moxifloxacin may also be utilized in this product as these formulations have very broad antibiotic coverage, pose minimum chances of bacterial resistance, and are very well tolerated by patients (Bloom P A et al. *Eur. J Ophthalmol.* 1994 4:6; Miller IM et al. *Am. J. Ophthalmol.* 1992 113:638; Gwon A. *Arch. Ophthalmol.* 1992 110:1234).

Antibiotic resistance has been reported with the use of Sulfonamides or Tetracycline, and as such these agents are usable but not preferred for this product in their present state (McCulley JP *Int. Ophthalmol. Clin.* 1984 24:65).

Method of Use

In a preferred embodiment, the product is a small, flexible eye pad that can fit within the peri-orbital region without substantially overlapping other skin. It is wrapped in a sterile wrapping. The user preferably cleans his/her hands before unwrapping the eye pad. Prior to use, and preferably while the eye pad is still wrapped, the user massages the container to mix the detergent, with or without antibiotic, mixture and "foam" the non-abrasive material that surrounds the heat pack. S/he then breaks the barrier between the two compartments by applying pressure, starting the exothermic reaction. If the cleanser and/or antibiotic are also contained in breakable compartments, this action will also release these components into the non-abrasive material on the eye pad. (If the cleanser and/or antibiotic are provided separately from the heat pack, the cleanser and/or antibiotic are applied to the material after removing the wrapper.)

The user then unwraps the eye pad, holds it by its handle (if provided), and gently massages the side of the eye pad having the cleanser and antibiotic around the affected peri-orbital region for a period of about 5-15 minutes as tolerated. After about ten to fifteen minutes, the user stops the treatment and discards the eye pad.

EXAMPLES

The following examples illustrate some embodiments of the invention.

Example 1

Construction of Product

A 2 inch by 2 inch by 3 inch flexible heat pack is obtained from, for example, Hospital Marketing Services (HMS) Co, Inc. The heat pack has two compartments, one containing magnesium sulfate in powder form, and the other containing water in an inner breakable plastic bag. A round hard plastic handle is attached to the pack on one end. The heat pack is covered with a soft, lint-free material, such as a layer of polyester and several layers of gauze. The gauze surrounding the heat pack is coated with a mixture of baby shampoo (Johnson & Johnson or Neutrogena) with or without Bacitricin Ophthalmic Ointment (E. Fougera & Co. Melville, New York) or Ciloxan Ophthalmic Solution (Alcon, Inc.) in an amount sufficient to transfer to the user's skin when the eye pad is being used. A removable piece of plastic is optionally placed over the coating to keep the coating in place. The eye pad is wrapped under sterile conditions in a plasticized paper covering which is easily removable by the user.

Example 2

Use of Product to Treat Chalazia

A patient presenting with a chalazion (stye) is advised to start using this product immediately after the onset of symptoms, and to follow up with his/her ophthalmologist as soon as possible. The patient foams the pack inside its sterile wrap and breaks the inner container by applying force. The patient then unwraps the heat pack, holds it by its handle. The patient then gently places the medicated side of the eye pad against the affected eyelid and moves the eye pad in small circles across the skin for ten minutes. When the treatment is finished, the patient disposes of the eye pad in the trash.

Example 3

Use of Product on Post-Surgical Wound

The procedures of example 2 are followed, except that the bandage is removed from the eye prior to treatment, and a clean bandage is reapplied to the eye after treatment.

What is claimed is:

1. An article of manufacture for treating the eye, comprising:
   an impermeable bag created by an impermeable membrane, the bag being sized to fit generally within a single peri-orbital region and sufficiently flexible to mold to the eye within the peri-orbital region without extending to the rest of the face;
   a material attached to the outside of the impermeable bag that is suitable for absorbing and retaining a liquid substance, and a substance suitable for cleaning eyelids present in said material, wherein the material does not cover the bag completely;
   a handle that is attached to the outside of the bag where the impermeable membrane is not covered; and
   a heat source that includes a liquid in the bag to produce an exothermic chemical reaction in the bag, the exothermic reaction to provide the bag with a temperature suitable for contact with eye lids, wherein the bag is impermeable in that the liquid of the heat source cannot pass outside the bag under ordinary use of the bag when heat is being released for treating the eye.

2. The article of manufacture of claim further comprising a wrapping in which the bag is held.

3. The article of manufacture of claim 2 wherein the material attached to the outside of the bag contains a detergent suitable for contact with eyelids.

4. The article of manufacture of claim 3 wherein the material attached to the outside of the bag contains an antibiotic suitable for eyelid treatment.

5. The article of manufacture of claim 1 wherein the bag contains two ingredients to produce the exothermic chemical reaction, the ingredients being liquid sodium acetate and stainless steel.

6. The article of manufacture of claim 1 wherein the cleaning substance is pH controlled so as not to cause ocular irritation.

7. The article of manufacture of claim 1, wherein the cleaning substance is an antibiotic solution suitable for use on eyes.

8. The article of manufacture of claim 1 further comprising an antibiotic substance for use on eyes present in said material.

\* \* \* \* \*